(12) United States Patent  
Godara

(10) Patent No.: US 7,163,536 B2  
(45) Date of Patent: Jan. 16, 2007

(54) DETERMINING CONNECTIONS OF MULTIPLE ENERGY SOURCES AND ENERGY DELIVERY DEVICES

(75) Inventor: Neil Godara, Mississauga (CA)

(73) Assignee: Baylis Medical Company Inc., Montreal (CA)

( * ) Notice: Subject to any disclaimer, the term of this patent is extended or adjusted under 35 U.S.C. 154(b) by 222 days.

(21) Appl. No.: 10/864,410

(22) Filed: Jun. 10, 2004

(65) Prior Publication Data

US 2005/0278007 A1   Dec. 15, 2005

(51) Int. Cl.  
*A61B 18/04* (2006.01)

(52) U.S. Cl. .............................. 606/34; 606/41; 606/42

(58) Field of Classification Search .................. 606/34, 606/39–40, 41–42  
See application file for complete search history.

(56) References Cited

U.S. PATENT DOCUMENTS

| | | | |
|---|---|---|---|
| 5,334,193 A | 8/1994 | Nardella | |
| 5,462,521 A | 10/1995 | Brucker et al. | |
| 5,688,267 A | 11/1997 | Panescu et al. | |
| 5,788,688 A * | 8/1998 | Bauer et al. | 606/1 |
| 5,800,432 A | 9/1998 | Swanson | |
| 6,017,338 A | 1/2000 | Brucker et al. | |
| 6,053,912 A | 4/2000 | Panescu et al. | |
| 6,235,022 B1 | 5/2001 | Hallock et al. | |
| 6,273,886 B1 | 8/2001 | Edwards et al. | |
| 6,500,175 B1 | 12/2002 | Gough et al. | |
| 6,506,189 B1 | 1/2003 | Rittman, III et al. | |
| 6,575,969 B1 | 6/2003 | Rittman, III et al. | |
| 6,702,810 B1 | 3/2004 | McClurken et al. | |
| 6,936,047 B1 * | 8/2005 | Nasab et al. | 606/34 |
| 6,939,346 B1 * | 9/2005 | Kannenberg et al. | 606/34 |
| 2005/0137662 A1 * | 6/2005 | Morris et al. | 607/101 |

* cited by examiner

*Primary Examiner*—Roy D. Gibson  
(74) *Attorney, Agent, or Firm*—Dimock Stratton LLP; Mark B. Eisen

(57) ABSTRACT

A method and system are disclosed for the mapping of energy delivery devices to energy sources. Energy capable of affecting a measurable property of the system is delivered through the energy delivery devices from the energy sources. A change in a property when the energy is delivered is measured using measuring devices that are associated in a known way with the energy delivery devices. A profile of the change is compared to a profile of the energy output in order to determine which energy sources produce an output capable of affecting the property measurable by each measuring device and, because of the association between measuring devices and energy delivery devices, each energy delivery device.

21 Claims, 5 Drawing Sheets

DETERMINING CONNECTIONS OF MULTIPLE ENERGY SOURCES AND ENERGY DELIVERY DEVICES

TECHNICAL FIELD

The invention relates generally to medical treatment devices in which multiple sources of energy may be coupled to multiple energy delivery devices. More particularly, the invention relates to determining the connections between the sources of energy and the energy delivery devices, where the connections are not permanent, and where the delivery of energy affects some measurable property.

BACKGROUND OF THE ART

When treating a tissue by applying energy to change one or more properties of the tissue, it is desirable to use a system that allows the measurement and modulation of those properties. For example, when applying energy to treat a tissue by heating, it is useful for the system to be able to measure the tissue temperature, and to regulate this temperature by controlling heating or cooling devices. Currently, many systems exist that are capable of this measurement and control.

Systems for treating tissue by applying energy typically comprise one or more energy sources connected to one or more energy delivery devices. A wide variety of devices for the measurement of tissue properties such as temperature, electrical potential, or impedance are also well known to those skilled in the art. The use of controlling systems to modulate temperature, potential, or impedance, for example, by controlling variables such as frequency, amplitude, voltage, or current delivered from an energy source through an energy delivery device, is also widely known and practiced by those skilled in the art. Besides directly controlling the energy applied to treat the tissue from a primary energy source, some systems control the supply of energy from an additional energy source; for example, systems that heat the tissue often use additional cooling means, whereby control of the level of cooling energy supplied is used to modulate the tissue temperature. Systems that use controlled cooling to modulate temperature are disclosed in U.S. Pat. Nos. 5,334,193; 5,462,521; 5,688,267; 5,800,432; 6,017,338; 6,053,912; 6,235,022; 6,273,886; 6,500,175; 6,506,189; 6,575,969; and 6,702,810.

When more than one energy delivery device is used to deliver energy from an energy source or sources to a tissue or more than one primary or additional energy source is used to control the energy delivered through an energy delivery device or devices, it is useful for the connections between energy delivery devices and energy sources to be known. That is to say, because the modulation is based on values provided by measuring devices associated with the one energy delivery devices, it is useful to know which energy sources are capable of providing energy to the energy delivery devices capable of affecting the given measurement. Incorrect mapping, which is a failure to correctly recognize which energy delivery devices correspond to which energy sources, can result in the delivery of energy through an energy delivery device other than that intended to be used, resulting in an unintended change in a tissue property. In order to prevent such problems, some current treatment systems use connectors that are colour coded, which have mating parts, or which are otherwise designed so that each energy delivery device is connected only to certain energy sources. This approach takes time to connect and to check, and requires that unique connectors be used for each pair or group of devices and sources to be connected. The use of unique connectors can reduce convenience or increase cost for the user or manufacturer, for example by requiring that a variety of parts be designed, manufactured and kept in stock. As well, visual matching of energy sources to energy delivery devices does not necessarily preclude improper connections from being made.

SUMMARY OF THE INVENTION

The invention provides a system and a method for mapping one or more devices capable of delivering energy, for example energy capable of modulating one or more properties of a tissue, to one or more sources of the energy.

One aspect of the invention provides a system for controlling the supply of energy produced by the energy source or sources. The system is coupled to the energy sources and operates to deliver energy from the energy sources to the energy delivery devices. The system is also coupled to one or more measuring devices associated with the energy delivery devices. The system comprises a mapping subsystem for determining which energy sources are connected to which energy delivery devices. Each respective energy source is operated to produce a distinct output profile. This output profile reflects a change over time in one or more property monitored by the system, for example a physical, chemical, electrical, or biological property, measurable by the measuring devices. Sequential production of energy by each energy source is one way to produce distinct output profiles; however the energy sources may also produce energy concurrently, provided that the output produced has a distinct, identifiable profile.

Once all of the energy sources have produced energy and the energy has been delivered through the energy delivery devices, changes in the property or properties are measured by the measuring device or devices. The measurements made by each measuring device, defining a respective response profile, are analyzed by the mapping subsystem, which matches the response profile(s) to the output profile(s) of one or more of the energy sources, or to none of the energy sources, thus mapping each energy delivery device known to be associated with the measuring device to the energy source or sources. The mapping subsystem may comprise a processor and a memory, whereby the memory stores instructions and data for controlling the processor.

The mapping sequence of: production of energy by the energy sources, delivery of energy by the energy delivery devices, detection by the measuring devices, and analysis by the controller, may be repeated one or more times before a final acceptance or rejection is produced. If there are subsequent repetitions of the sequence, the output profile of any or all of the energy sources may be modified from one repetition to another. Modification of the output profile, for example to increase the overall intensity or to change the shape of energy output vs. time, may increase the ability of the output to be detected or distinguished, and thus increase the chances that one of the energy delivery devices can be mapped to it.

Another aspect of the invention provides a system for delivering energy using one or more energy sources coupled to one or more energy delivery devices via unknown connections, whereby the system is capable of mapping the energy delivery device(s) to the energy source(s). As described in the embodiment above, the energy sources are capable of producing energy according to distinct output profiles, said energy able to be delivered through one or more of the energy delivery devices via the unknown connections. Measuring devices, as described above are connected to a controller within the system. The controller serves to control the one or more energy sources and to map energy delivery devices to energy sources, as described above.

A further aspect of the invention provides a method for mapping one or more energy delivery devices to one or more energy sources. The method includes the step of outputting energy from the energy source(s) according to distinct output profiles, as defined above. The energy output by the energy source(s) is delivered through the energy delivery device(s), which are connected to the energy source(s) via unknown connections. Upon delivery of energy from an energy delivery device, changes in a measurable property resulting from the delivery of energy are measured to determine a response profile for each energy delivery device. The response profiles are compared to the output profiles, as described above, thus mapping the energy delivery device(s) to the energy source(s). Other aspects including computer program product aspects will be apparent to those of ordinary skill in the art.

The correct association between energy sources and measuring devices will ensure that a measurement made by a measuring device, which indicates that a tissue property needs modulation, will trigger a response by an energy source capable of affecting the property through the correct energy delivery device. Mapping prevents potentially dangerous situations whereby a modulating signal is produced where none is required, or whereby no modulating signal is produced where one is required. As well, automatic mapping of energy delivery devices to energy sources eliminates the need for the use of different components that physically, visually, or otherwise facilitate accuracy and identifiably of connections. Automatic mapping is thus more convenient, and allows for a greater universality of components.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

In accordance with an aspect of the invention a system for mapping energy delivery devices to energy sources is provided.

Figure 1:
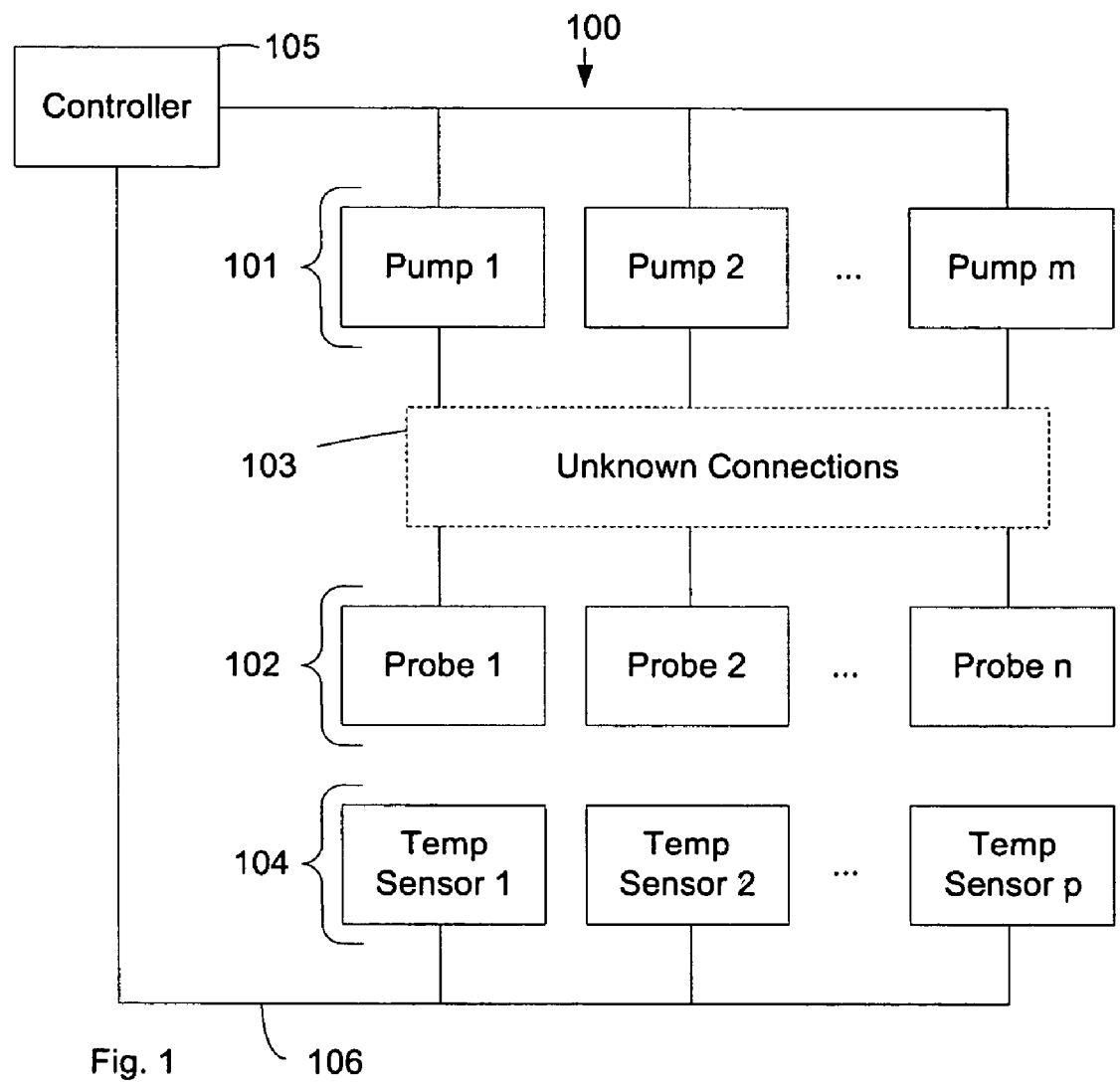
FIG. 1 is a block diagram showing components of a mapping system in accordance with a first embodiment of the invention.

Aspects of the invention include a system and a method for mapping a number of internally cooled probes to a number of pumps. There is shown in FIG. 1, a first embodiment of a system 100 that uses one or more pumps 101 to control the movement of a cooling fluid medium which is capable of removing thermal energy from one or more internally cooled probes 102, or from tissue surrounding the probe(s). Although the pumps 101 are used to remove energy, their purpose may be generalized as energy sources such as energy sources 106 shown in a second embodiment of the invention of FIG. 1B in that they are capable of working to change the energy of a probe 102 or tissue. In any embodiment whereby the energy is delivered to a tissue, as in the preferred embodiment, the system is intended to include the tissue, for the purposes of a delivery of energy that results in a change in a property of the system.

Pumps 101 are coupled to probes 102 via releasable connections 103. Each connection 103 typically comprises a tube or other conduit for carrying the cooling medium and at least one enclosed tube has a connector adapted from releasable connection to a probe 102 or a pump 101. The other end may have a releasable connection for attaching to the other end of the pump and the probe; however, the connection may be fixed. In accordance with a particular arrangement of an aspect of the invention, connections 103 may be determined.

Probes 102, which are capable of being inserted into the body, act as energy delivery devices such as devices 107 of the second general embodiment shown in FIG. 1B, circulating the cooling fluid supplied by the pumps 101. In a further embodiment (not shown), the probes 102 are furnished with electrodes or heating elements for ablating tissue.

Figure 2:
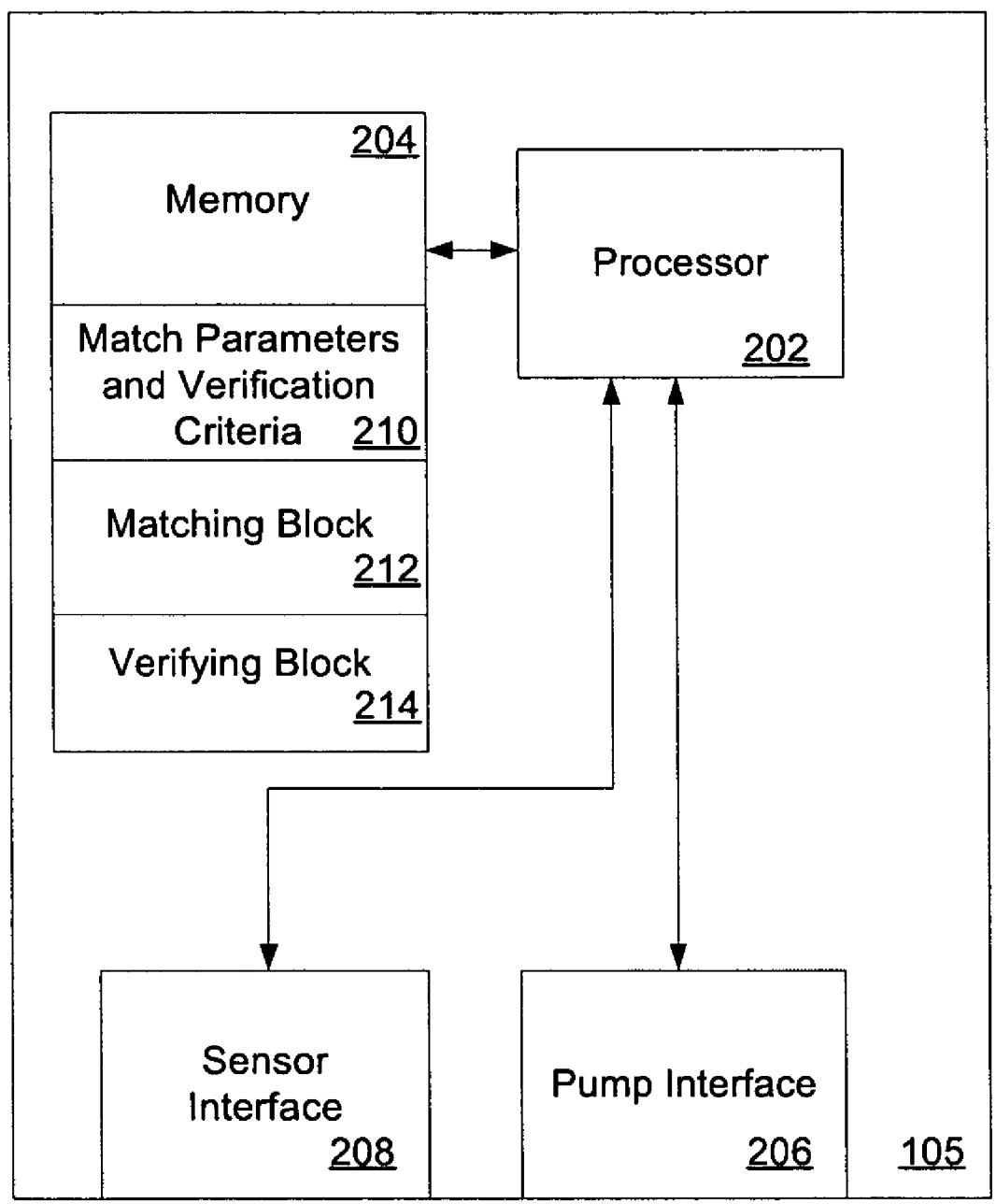
FIG. 2 is a block diagram of an exemplary controller for mapping a system in accordance with the embodiment of the invention.

The probes 102 are associated with temperature sensors 104, which may be carried by the probes 102 themselves, or may be self-contained and separate from the probes 102, so long as the sensors 104 are capable of sensing changes in temperature caused by the removal of thermal energy by the probes 102. The temperature sensors 104 are connected, via electrical connections 106 to a central controller 105, which receives and analyzes the temperature information. The controller 105 is responsible for controlling the operation of the pumps 101 in accordance with output profiles. Controller 105 operates the pumps 101 to modify the output profile based on temperature information received from the temperature sensors 104. FIG. 2 is a block diagram of a software programmable embodiment of a controller 105. Controller 105 comprises a processor 202 coupled to a memory store 204 (e.g. a ROM, a RAM, a flash memory device or a combination thereof) which stores instructions and data for controlling the operations of processor 202. Processor 202 is also coupled to a pump interface 206 for controlling the operations of pumps 101 and a sensor interface 208 for receiving temperature measurements from temperature sensors 104. Memory 204 stores instructions for performing matching operations (matching block 212) and for verifying the match results (verifying block 214) as well as tuneable parameters and thresholds and verification criteria 210 for use by the instructions 212, 214. Persons of ordinary skill in the art will appreciate that additional instructions may also be present (not shown) such as one or more of an operating system, a communication system and user interface instructions, among others. As well, controller 105 may additionally comprise components such as one or more I/O interfaces, power sources, etc.

In the system 100 described above, the connections 103 between pumps 101 and probes 102 are not permanent. This flexibility allows for a variable number of pumps 101 and a variable number of probes 102 to be used, and allows for any pump 101 to be connected to one or more probes 102 or for any probe 102 to be connected to one or more pumps 101. Because these connections are not permanent, a determination must be made, prior to treatment, of the specific configuration of the system so that if a region of tissue capable of being cooled by a certain probe 102 requires cooling during treatment, controller 105 can operate an appropriate pump 101 capable of supplying cooling fluid to that probe 102. While the present system can be used in conjunction with tubing 103 that visually indicates (for example, by using colour), or physically restricts (for example by using shaped mating connectors) the connections, it is also intended to be able to be used as the sole mode of determining the connections between pumps 101 and probes 102.

Figure 3:
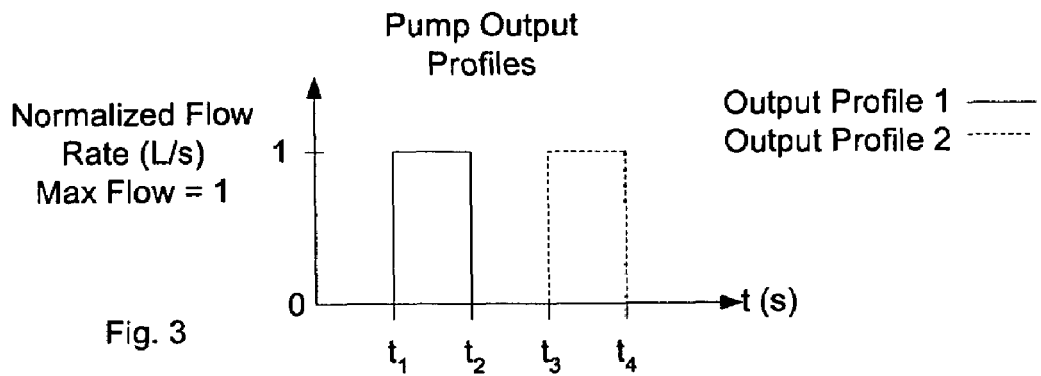
FIG. 3 is an exemplary graph showing two output profiles that may be produced in accordance with the first embodiment of the invention.
Figure 4:
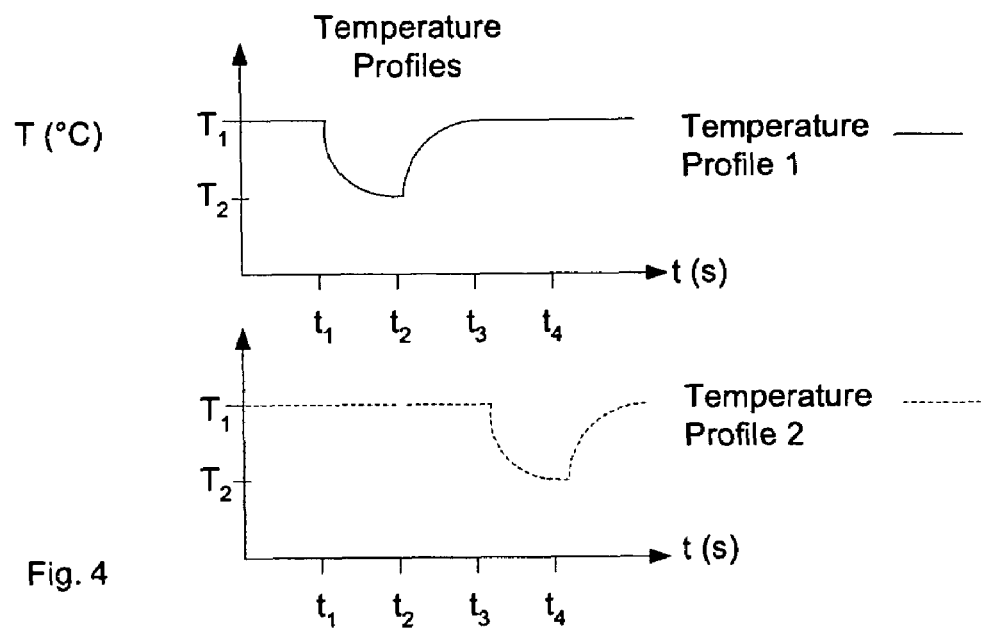
FIG. 4 is an exemplary graph showing two temperature profiles, which correspond to the output profiles of FIG. 3, and which may be produced in accordance with the first embodiment of the invention.

In accordance with a method aspect, the controller 105 sends a signal to modify a pump rate to produce a specific output profile. As shown in FIG. 3, the shape of the output profile is a representation of a pump's flow rate with respect to time. Each pump 101 pumps cooling fluid according to its respective output profile. The temperatures of the probes 102 change correspondingly. The changes in temperature with time produce a characteristic shape, or temperature profile. FIG. 4 shows possible temperature profiles that correspond to the output profiles shown in FIG. 3. The temperature profile is measured by one or more temperature sensors 104 and is communicated to the controller 105 through electrical connections 106. Persons of ordinary skill in the art will appreciate that a variable number of temperature sensors 104 may be used to detect the temperature profile of a probe 102. As well, one temperature sensor 104 may be used to detect the temperature profiles of more than one probe 102. In order for mapping to occur, however, it is necessary that the relationships between temperature sensors 104 and probes 102 be known, so that any match made between the temperature profile measured by a temperature sensor 104 and an output profile produced by one or more pumps 101 will necessarily correspond to a relationship between particular probe or probes 102 and particular pump or pumps 101. This matched relationship represents a mapping of probes 102 to pumps 101. In a preferred system 100, individual temperature sensors 104 are mounted on respective probes 102 giving a known and permanent relationship for the purposes of mapping.

Controller 105 performs matching operations to match temperature profiles and pump output profiles. Preferably, such operations may be directed by software stored or otherwise communicatively coupled to controller 105. Operations may be adjusted or tuned through variable tolerances. The tolerances may be manually or automatically tuned to control matching. For example for any given output profile, the tolerances for: magnitude of temperature change for any given change in pump rate, delay before change is observed, and, rate at which change occurs, are among the tolerances that can be controlled.

Figure 5:
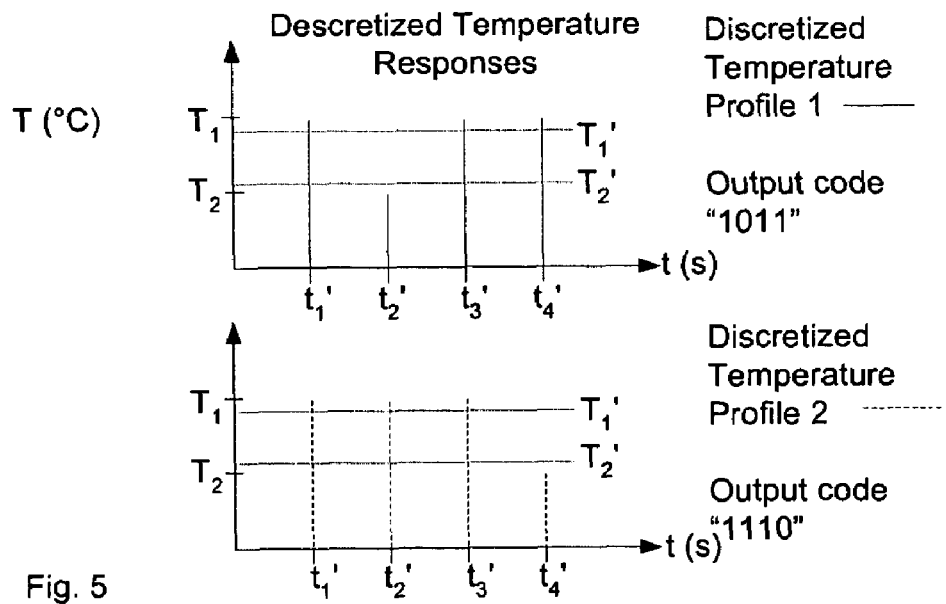
FIG. 5 is an exemplary graph showing discretized temperature responses, which correspond to the temperature profiles of FIG. 4, and which are encoded according to the first embodiment of the invention.

In the preferred embodiment, temperature measurements are taken periodically (e.g. $t_1'$, $t_2'$, $t_3'$, and $t_4'$ in FIG. 5) in accordance with a pre-determined time interval, $\Delta t_\alpha$, before or after times at which changes occur in the output profile (e.g. $t_1$, $t_2$, $t_3$, and $t_4$ in FIG. 2). In the example of FIGS. 2, 3, and 4, FIG. 5 shows the discrete temperature responses at times $t_1'$, $t_2'$, $t_3'$, and $t_4'$ for each of the temperature profiles shown in FIG. 4. Variable temperature thresholds are set, within the controller, above or below which the discrete temperature response at given $t_n'$ is assigned a certain digitized value. In the example of FIG. 5, any response with a value above temperature threshold $T_1'$ is assigned a value of 1 and any response with a value below temperature threshold $T_2'$ is assigned a value of 0. Thus, the measurements made by one temperature sensor are translated from a graphically representable set of measurements or temperature profile, as in FIG. 4, into a digitized output code, as in FIG. 5. As shown in FIG. 5, the measurements made by temperature sensor 1 correspond to the output code 1011 and the measurements made by temperature sensor 2 correspond to the output code 1110. The temperature thresholds ($T_1'$, $T_2'$ or $T_n'$ generally) may be adjusted up or down in order to adjust the sensitivity of the digitization. The resulting output codes are compared to expected codes for each output profile. Comparing FIGS. 3, 4, and 5, output profile 1 has an expected code of 1011 and output profile 2 has an expected code of 1110; thus, output profile 1 corresponds to temperature profile 1 and output profile 2 corresponds to temperature profile 2. In another embodiment, the temperature thresholds $T_n'$ can depend on the maximum and minimum temperature values of the temperature profiles, for example with a threshold $T_1'$ being a predetermined value, $\Delta T_\beta$ below the maximum measured temperature $T_1$.

Matching the output profile of a pump 101 to the temperature profile of a temperature sensor 104 matches that pump to that sensor. Because the temperature sensors 104 are associated in a known way with the internally-cooled probes 102, the results of the matching operations show, for each temperature sensor 104, which pumps 101 are capable of supplying energy to change the temperature of the probes 102 associated with that sensor 104. That is to say, the matching operations map the probes 102 to the pumps 101. A probe 102 can be mapped to one or more pumps 101, or can be mapped to no pumps.

The mapping results of the matching operations, for each temperature sensor (and its associated probes), may be verified by controller 105. For any set of m pumps and p temperature sensors 104, there will be a set of possible results mapping the sensors 104 to the pumps 101 given by the equation: $(mC0+mC1+ \ldots +mCm)^\wedge p$, where C represents the Choose function whereby $xCy=x!/(x-y)!y!$. For an embodiment having two pumps 101 and two temperature sensors 104, there are 16 possible mapping outcomes as shown in the following table:

Set of Possible Results for Mapping Two Pumps to Two Temperature Sensors:

|  | Temperature Sensor 1 | Temperature Sensor 2 |
| --- | --- | --- |
| 1) | Pump 1 | Pump 1 |
| 2) | Pump 1 | Pump 2 |
| 3) | Pump 1 | Pumps 1 and 2 |
| 4) | Pump 1 | No Pumps |
| 5) | Pump 2 | Pump 1 |
| 6) | Pump 2 | Pump 2 |
| 7) | Pump 2 | Pumps 1 and 2 |
| 8) | Pump 2 | No Pumps |
| 9) | Pumps 1 and 2 | Pump 1 |
| 10) | Pumps 1 and 2 | Pump 2 |

-continued

|  | Temperature Sensor 1 | Temperature Sensor 2 |
|---|---|---|
| 11) | Pumps 1 and 2 | Pumps 1 and 2 |
| 12) | Pumps 1 and 2 | No Pumps |
| 13) | No Pumps | Pump 1 |
| 14) | No Pumps | Pump 2 |
| 15) | No Pumps | Pumps 1 and 2 |
| 16) | No Pumps | No Pumps |

Controller 105 performs verifying operations either accepting or rejecting the combined mapping from the matching operation. Utilizing software, such as a verifying block 214 with predefined comparative mapping, verification criteria 210 can be changeable and will depend on the requirements of the treatment or system. Any particular mapping result or any group of mapping results may be chosen as comparative mappings to define verification criteria 210 as a basis for accepting or rejecting the combined mapping from the mapping operation, such as, for example, rejecting any mapping result where a temperature sensor 104 is not mapped to any pump 101. As well, if the controller rejects the mapping determined by the mapping operations, the specific results of the matching operations can be used to modify the output profile of the pumps 101 during repetitions of the mapping operations, if any. For example, if the verifying block 214 requires that every pump 101 be matched to a different temperature sensor 104, then the output profile of an unmatched pump 101, or a pump 101 that is matched to multiple temperature sensors 104 can be modified to make it more distinguishable (e.g. by increasing the magnitude of the changes in pump rate, or by separating it from other output profiles in time). Characteristics of the matching operations can also be changed depending on the results of the verification operation. For example, if a temperature sensor 104 is shown to be matched to more than one pump 101, in a situation where each temperature sensor 104 is required to be connected to only one pump 101, decreasing the tolerance of the matching operation to changes in temperature 210 can allow the correct match to be determined above any background temperature fluctuation.

Figure 6:
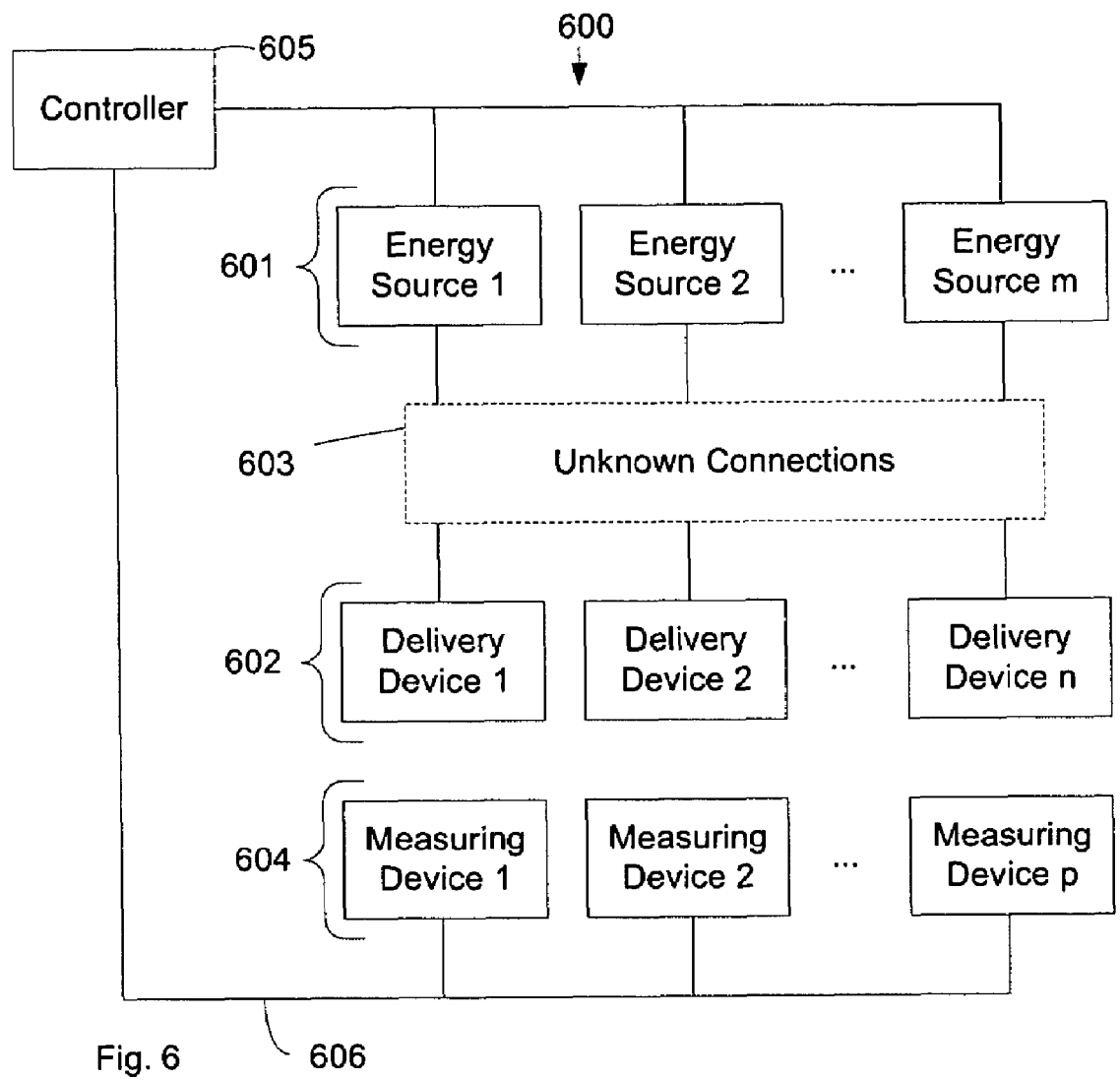
FIG. 6 is a block diagram showing components of a mapping system in accordance with a second embodiment of the invention.

Referring to FIG. 6, there is shown a system 600 according to a generalized embodiment similar to FIG. 1. A wide variety of devices are used as energy sources 601, energy delivery devices 602 and measuring devices 604 in systems that treat tissue by applying energy and the invention described above is intended to encompass automatic mapping to determine connections 603 between energy delivery devices 602 and/or measuring devices 604 to energy sources 601 for any and all such systems, and any methods for such mapping. Additionally, while systems for controlling the output from the energy source or sources 601, receiving input from the measuring devices 604 via connections 606, and mapping the energy delivery devices 602 to the energy sources 601, are all considered to be components of the controller 605, they are not required to be collected within one self-contained device.

Figure 7:
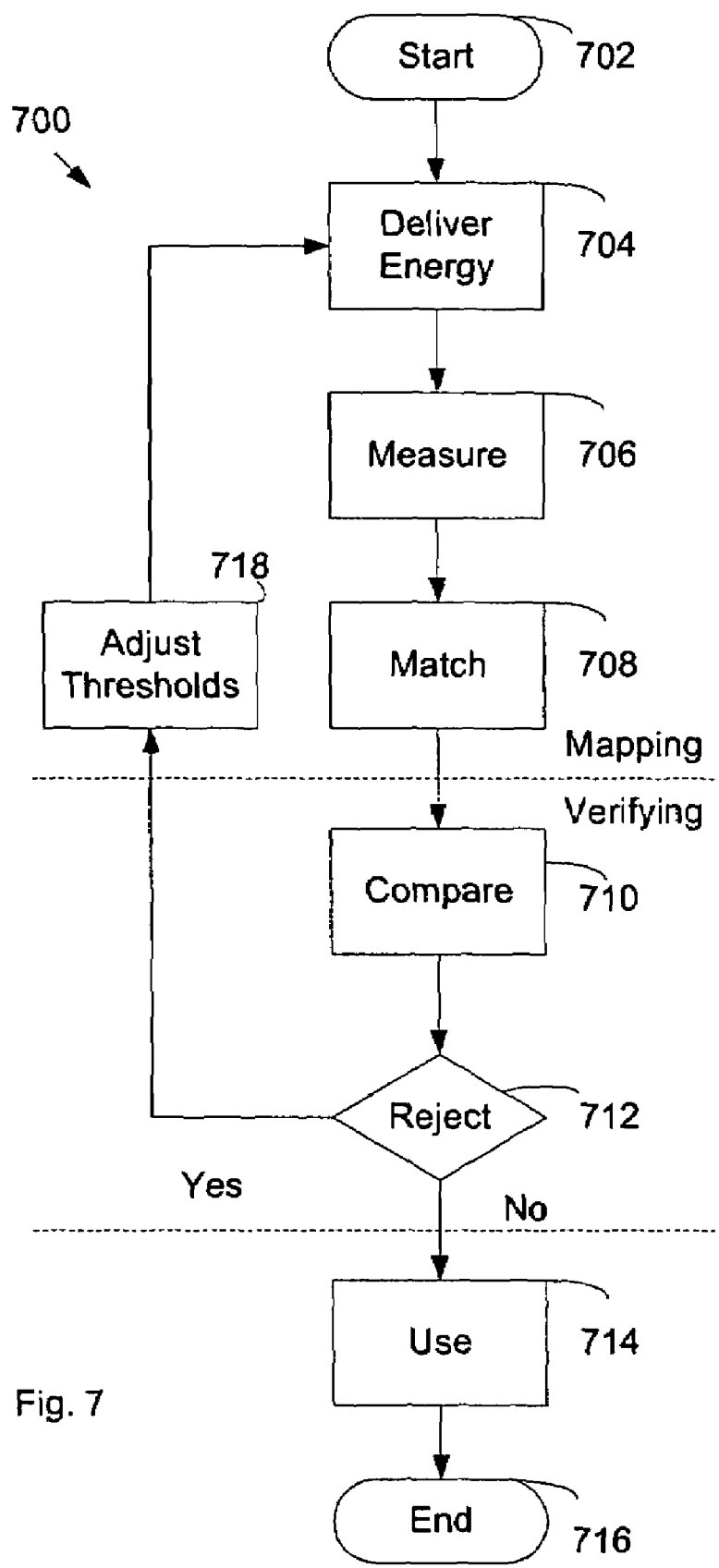
FIG. 7 is a flowchart of operations for mapping in accordance with an embodiment of the invention.

FIG. 7 is a flowchart of operations 700 for mapping energy sources to energy delivery devices in accordance with an embodiment of the invention for a system to be mapped such as system 600. Commencing at start 702, such as following the initial assembly and general set up of the system 600, operations 700 initiate a matching phase and proceed to a verifying phase. In response to the verifying phase, mapping operations 700 may loop back to the matching phase or continue to a use phase.

More particularly, at step 704, controller 605 operates the energy sources 601 to deliver energy to the energy delivery devices 602 via unknown connections 603. In response, the measuring devices 604 associated with the energy delivery devices 602 in some known manner measure a response to the energy delivered and provide the measured response to the controller 115 (step 706) via connections 606. Though steps 704 and 706 are shown as complete, sequential steps, persons of ordinary skill in the art will appreciate that steps 704 and 706 may be repeated for each of energy sources 601 to be mapped or in other manners in accordance with a test procedure.

At step 708, controller 605 matches the energy sources 601 to the delivery devices 602, as described previously, such as by matching output profiles to measured response profiles, for example temperature profiles. At step 710, controller 605 compares the match results to verify that the respective associated energy sources 601 and delivery devices 602 accord with verification criteria as previously described. At step 712, if the match is accepted (i.e. not rejected), via No branch to step 714, operations may proceed to a use phase and thereafter end (step 716). At step 712, if the match is rejected, via Yes branch to step 714, operations may proceed back to the matching phase, such as to step 718 where tuneable parameters (e.g. various thresholds) may be adjusted. Persons of ordinary skill in the art will appreciate that this step is optional. Moreover, though not shown, the system 600 to be mapped may be otherwise manipulated, for example, repositioning energy delivery devices 602 or measurement devices 604 or adjusting connections 603. Steps 704-712 are then preferably repeated as necessary. Alternatively the operations may end at step 712 if, after a predetermined number of repetitions of steps 704–712 the match is rejected, and a message may be displayed stating that mapping has failed (not shown).

Although the system and method described herein is described in relation to mapping energy delivery devices to sources of energy in the form of cooling carried by a fluid medium, any form of energy, including but not limited to: electrical current or potential, thermal energy, pressure, or magnetic forces may be added or removed and be considered to be within the scope of this invention. Those skilled in the art will appreciate that many tissue properties, both physical and chemical, including but not limited to: temperature, impedance, electrical potential, pressure, density, and opacity can be modulated by a system using energy delivery devices automatically mapped to energy sources, and that such a system has application in any tissue of the body.

The embodiment(s) of the invention described above is(are) intended to be exemplary only. The scope of the invention is therefore intended to be limited solely by the scope of the appended claims.

I claim:

1. A system for controlling the delivery of energy from two or more energy sources coupled to two or more energy delivery devices via unknown connections, the system comprising:

a) an energy source interface for coupling said energy sources to the system for operation to deliver energy using the energy delivery devices, said energy delivery devices associated with one or more measuring devices for measuring a result of the delivery of energy;

b) a measuring interface for coupling said measuring devices to said system to obtain measurements of the result; and c) a mapping subsystem for determining an association between the energy sources and energy delivery devices thereby to control the delivery of energy to the energy delivery devices.

2. The system of claim 1 wherein the mapping subsystem comprises a processor and a memory storing instructions and data for controlling the processor, said instructions and data adapting the processor to match said energy sources to said energy delivery devices in response to operating the energy sources and measuring the result.

3. The system of claim 2 wherein the system operates each energy source in accordance with a respective output profile and receives measurements defining a respective response profile and wherein said mapping system comprising a matching component to match the output profiles and response profiles to determine the association between the energy sources and energy delivery devices.

4. The system of claim 2 wherein said mapping system comprises a verifying component to verify the association between the energy sources and energy delivery devices.

5. The system or claim 1, wherein the energy supplied by the two or more energy sources is capable of modulating one or more properties of a tissue.

6. The system of claim 5 wherein at least one of the energy sources comprises a pump for pumping a cooling fluid medium.

7. The system of claim 5 wherein at least one or the energy delivery devices comprises an internally cooled probe capable of being inserted into a body of a patient.

8. The system of claim 7 wherein the probe includes an electrode for ablating the tissue.

9. The system of claim 1 wherein the one or more measuring devices are coupled to the two or more energy delivery devices.

10. The system of claim 1 wherein the system comprises a controller contained within a single device.

11. A system for delivering energy using two or more energy sources coupled to two or more energy delivery devices via unknown connections, the system mapping the two or more energy delivery devices to the two or more energy sources, the system comprising:

a) the two or more energy sources, each energy source capable of producing energy according to an output profile that is distinct from the output profiles of each other energy source;

b) the two or more energy delivery devices, each delivery device connected to one or more of the energy sources for delivering the energy;

c) one or more measuring devices for measuring changes in a property resulting from the delivery of the energy; and d) a controller connected to the one or more measuring devices and to the two or more energy sources for controlling the two or more sources and for mapping energy delivery devices to respective energy sources by matching the output profiles with the changes.

12. A method for mapping two or more energy delivery devices to two or more energy sources comprising the steps of:

a) outputting energy from the two or more energy sources, each energy source producing an output profile that is distinct from the output profiles of each other energy source;

b) delivering the energy through the two or more energy delivery devices connected to the energy sources;

c) measuring changes in a property resulting from delivery of the energy to determine a response profile for each delivery device; and d) mapping energy delivery devices to respective energy sources by matching the output profiles and response profiles.

13. The method of claim 12, wherein the step of delivering the energy modulates one or more properties of a tissue.

14. The method of claim 13 wherein at least one of the energy sources comprises a pump for pumping a cooling fluid medium.

15. The method of claim 13 wherein at least one of the energy delivery devices comprises an internally cooled probe capable of being inserted into a body of a patient.

16. The method of claim 15 wherein the probe includes one or more electrodes for ablating the tissue.

17. The method of claim 12 wherein the method is used in a treatment of intervertebral discs.

18. The method of claim 12 wherein each of the two or more energy delivery devices comprises at least one measuring device for measuring said changes.

19. the method of claim 12 wherein mapping comprises matching the profiles and verifying a result of said matching.

20. The method of claim 12 comprising adjusting a threshold parameter for controlling the mapping.

21. The method of claim 12, comprising repeating the steps of the method to obtain a correct mapping.

* * * * *